United States Patent [19]

Larson et al.

[11] 4,251,219
[45] Feb. 17, 1981

[54] APPARATUS FOR AND METHOD OF DETERMINING CONTAMINANTS ON LOW PRESSURE CONDENSATE

[76] Inventors: Thurston E. Larson, 706 La Sell Dr.; Russell W. Lane, 1207 Devonshire Dr.; Chester H. Neff, 1808 Broadmoor Dr., all of Champaign, Ill. 61820

[21] Appl. No.: 955,914

[22] Filed: Oct. 30, 1978

[51] Int. Cl.³ .................... G01N 27/46; G01N 33/18; G05D 9/00
[52] U.S. Cl. ................................ 23/230 R; 210/662; 210/664; 422/68; 422/106
[58] Field of Search .................... 422/68, 76, 106; 23/230 R; 210/25, 26, 33; 324/30 R; 202/83, 206; 203/DIG. 7

[56] References Cited
U.S. PATENT DOCUMENTS

| | | | |
|---|---|---|---|
| 2,832,673 | 4/1958 | Larson et al. | 23/230 R |
| 3,158,444 | 11/1964 | Larson et al. | 210/33 |
| 4,052,267 | 10/1977 | McFee | 202/83 |

Primary Examiner—Michael S. Marcus
Attorney, Agent, or Firm—Charles H. Brown

[57] ABSTRACT

Measurement is made of low levels of chloride, sulfate, phosphate, nitrate and other inorganic anions in a relatively low pressure condensate having a temperature preferably below 40° C. The condensate is passed through a hydrogen exchange resin bed and the effluent from the resin bed is heated to atmospheric boiling temperature to eliminate gases such as carbon dioxide and ammonia. Heat to maintain a constant atmospheric boiling temperature is supplied by an electric heating element. A temperature sensor on the influent test water adjusts the voltage or current supplied to the electric heating element to maintain the constant atmospheric boiling temperature. A fail-safe device prevents electric heater failure on water flow stoppage. The conductivity of the heated water at or very close to atmospheric boiling point temperature is measured and is an indication of the contamination present in the relatively low pressure, low temperature test condensate.

18 Claims, 1 Drawing Figure

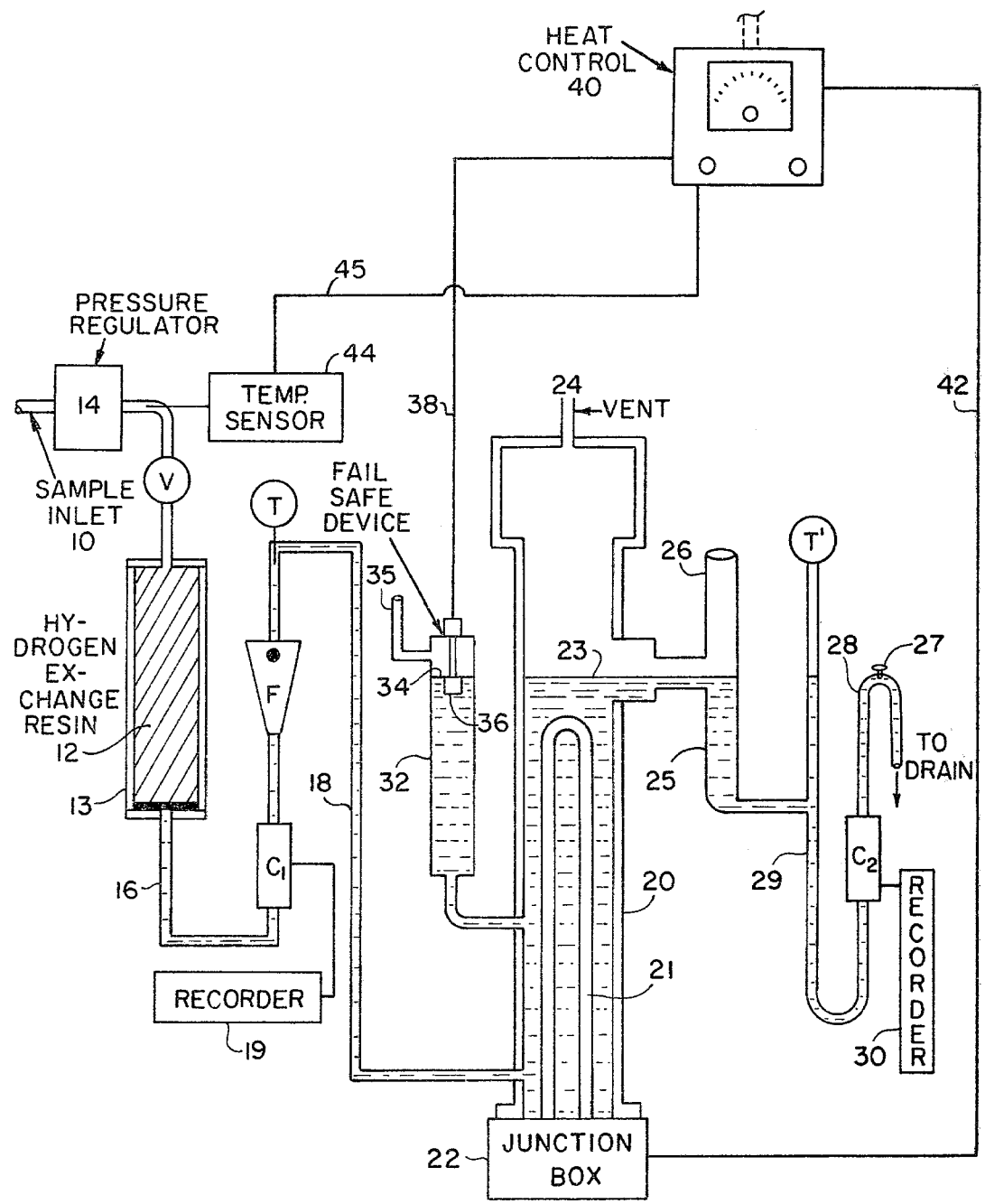

APPARATUS FOR AND METHOD OF DETERMINING CONTAMINANTS ON LOW PRESSURE CONDENSATE

This invention relates to a method of and apparatus for testing the purity of condensate in boiler systems, such as steam power plants, and in PWR (pressurized water reactor) nuclear systems.

BACKGROUND OF INVENTION

A troublesome problem presently existing in the power industry is the presence of contaminants which pass into the condensate due to the leakage of cooling water in steam power plants. This condensate, after passing through the turbine, is usually at a temperature below 40° C., for example 30° C., and at a pressure usually under 100 lbs psi (per square inch) and returns to the steam generator. It is important that the condensate returning to the steam generator be free of contaminants. These contaminants in the leakage water are the chlorides, sulfates, phosphates and nitrates which may cause mechanical failures, such as boiler tube eruption, corrosion and cracking of turbine blades, undesired deposits, and deterioration of auxiliary equipment.

The failure of some boiler systems, as for example in PWR nuclear systems, may be highly dangerous to operating personnel by exposure to radiation. The shutdown of any power plant due to the above mentioned problem may injure personnel and cause serious economic loss to the community serviced by the plant.

So far as applicants are aware, there is no presently known apparatus for determining the degree or extent of contamination in the condensate due to leakage in steam power plants on a continuous measuring basis. The present invention provides such apparatus and fulfills a need sought by the power industry.

OBJECTS AND FEATURES OF INVENTION

An object of the invention is to enable the detection of low level (of the order of 5 to 10 ug/l) chloride, sulfate, phosphate and nitrate in relatively low pressure (of the order of 100 lbs psi and below) condensate at temperatures below approximately 40° C. in cooled condensate present in boiler systems and in PWR (pressurized water reactor) nuclear systems.

A further object is to provide continuous sensitivity measurements of chloride, sulfate, phosphate, nitrate and other anions present in relatively low pressure, relatively low temperature (approximately 40° C. and below) condensate, and of an accuracy greater than heretofore possible.

An advantage of the present invention is that it employs electricity for heating rather than steam. The resulting structure is relatively light in weight, relatively compact, and portable for easy movement to localized areas of the power plant suspected of providing leakage water contamination to the condensate. It is versatile in that it can be located or moved to test water at various localized areas of a turbine condenser, and to condensate polisher influent and effluent, deionizer or importantly to various cooled samples piped to the laboratory. By sampling localized areas of a condenser which are suspected of providing inorganic contamination, extreme sensitivity in detection of the contaminant is attained.

Other objects, features and advantages will appear from a reading of the detailed description of the invention which is given in conjunction with a drawing, the single FIGURE of which is a diagram, partly in section, showing the apparatus of the invention for carrying out our method for testing the purity of condensate.

BRIEF SUMMARY

Briefly stated, the invention detects and measures low levels of chloride, sulfate, phosphate, nitrate and other inorganic anions in relatively low pressure condensate having a temperature below 40° C. The condensate passes through a hydrogen exchange resin bed and the effluent from the resin bed is heated to atmospheric boiling temperature to eliminate gases such as carbon dioxide and ammonia. Heat to maintain a constant atmospheric boiling temperature is supplied by an electric heating element. A temperature sensor on the influent test water adjusts the voltage or current supplied to the electric heating element to maintain the constant atmospheric boiling temperature. A fail-safe device prevents electric heater failure on water flow stoppage. The conductivity of the heated water at or close to atmospheric boiling point temperature is measured and is an indication of the contamination present in the relatively low pressure condensate.

DETAILED DESCRIPTION

A detailed description of the apparatus and the operation of the invention will now be given. A sample of the condensate at a temperature of approximately 40° C. and lower (for example 30° C.) and at a relatively low pressure (for example 100 lbs psi) is supplied by inlet 10 such as any suitable pipe or conduit, to the hydrogen exchange resin 12, preferably through a pressure regulator 14 and through a valve V. The valve V is a flow regulating valve which is adjusted to maintain through it a flow of sample fluid as constant as possible as pressure inlet conditions may vary. The pressure regulator 14 assures a more constant flow rate through the entire apparatus. The flow rate may be of the order of 175 ml/min (mililiters per minute). The sample condensate may be contaminated by leakage water from pipes in the power system. The location at which the sample is taken and the location of the instrument of the invention is flexible and may be at localized areas of the condensor which are suspected of providing inorganic contamination to the condensate, or at locations before or after a condensate polishing operation is effected. The resin bed 12 is preferably contained within a transparent chamber 13, such as clear lucite, to enable operating personnel to observe the color of the hydrogen exchange resin bed for ascertaining when the bed is exhausted and requires replacement.

The hydrogen exchange resin 12 removes amine contaminants such as ammonia and converts inorganic salts to acid form, which is more conductive. One type of hydrogen exchange resin is a strong type cation exchange resin, such as polystyrene material sold by Rohm & Haas as IR-120 in hydrogen form.

The effluent from the resin bed 12 is passed through a tube 16 to a flow type conductivity cell C1 and then through a flowmeter F from which the condensate is passed on through tube 18 to an electric reboiler 20. Cell C1 is connected to a recorder 19 which indicates the cation conductivity of the sample condensate after passing through the resin bed. The conductivity cells and the recorders may be of the type sold by Beckman Instruments, Inc. of Fullerton, Calif. The flowmeter used in the practice of the invention is known by the trade-name Rotameter or Flowmeter and is sold by Rotameter Company of Lansdale, Pa. Flowmeter F is set at a flow that minimizes leaching from the hydrogen exchange resin bed while making optimum utilization of the resin bed. Thermometer T registers the temperature of the liquid in tube 18 before the water passes into the electric reboiler 20.

Electric reboiler 20 enables a determination of a constant temperature, and also assures the removal of carbon dioxide from the boiling water in reboiler 20, thereby assuring continuous accurate measurements at boiling water temperature under more favorable pH conditions. The electric reboiler is provided with an electric heating element 21 which raises the temperature of the water flowing into reboiler 20 to atmospheric boiling water temperature. Heating element 21 is a hairpin or U-shaped stainless steel sheath which encloses an electric heating wire, in turn, electrically connected to a junction box 22. The smooth continuous boiling of the water in the reboiler 20 drives off, through vent 24, the carbon dioxide in the water, which flow out of the reboiler in the degassifying process. Tube 26 provides an outlet for flash steam and air bubbles which may be generated in the boiling water and which may tend to obstruct the flow of water from reboiler 20 into tube 29.

The boiling water in reboiler 20 passes through tubes 25 and 29 to a flow type conductivity cell C2 from which the heated water flows out of a tube 28 of adjustable height at its overflow end to a drain. If desired, tube 29 may connect to the bottom of tube 25 in one straight line therewith. The height of tube 28 is on the level of the heated water in reboiler 20 and is adjusted to provide a constant water lever 23 for the water in the reboiler. A screw 27 which enters the top of tube 28 serves as a siphon breaker. A thermometer $T^1$ at the top of tube 29 measures the temperature of the water in this tube and indicates whether or not the effluent from the reboiler 20 is at atmospheric boiling temperature.

Cell C2 is connected to a recorder 30 which detects the degree of impurities (chloride, sulfate, nitrates) in the condensate sample which had been fed to the hydrogen exchange resin bed 12. The recorder can be of a type which subtracts the conductivity of pure water (0.82, US/cm at 98.5° C.) from the conductivity measurement of cell $C_2$, thereby indicating the chloride and sulfate content.

A chamber 32 in fluid communication with the interior of the reboiler 20 has a water level 34 which, in normal satisfactory conditions of operation, is at the same level as 23 in the electric reboiler. If the lever 34 drops below 23 a sensor or float 36 will, by means of electrical connection 38, actuate a relay in heat control equipment 40 to shut off the electrical power to the heating element 21, via electrical lead 42, thereby preventing electrical failure of the heating element 21, for the reboiler 20 on water flow stoppage. Hence, chamber 32 and sensor 36 taken together can be considered a fail-safe device. The flow rate can vary, for example, from 20 to 30 lbs. per hour without effecting the level 23. If the flow rate is too high, then water will overflow from overflow or waste tube 28 and pass down the drain. If the flow rate is too low, then the water level 23, as a result of the boiling process, will drop and cause the actuation of the fail-safe device. A vent 35 serves to exit water from the fail-safe device when the level 34 exceeds the level 23.

A temperature sensing device 44 coupled to the influent condensate test water at a location between the pressure regulator 14 and valve V is connected also, via lead 45, to the heat control equipment 40 to regulate the voltage or the current flowing to the input of the heating element 21 to thereby assure the proper heat for constant atmospheric boiling temperature in the reboiler 20.

The apparatus of the invention is designed to provide a constant flow of test influent condensate water, smooth continuous rate of boiling to remove gases, proper steam-water separation, prevention of steam and air bubble interruption of flow on passage through conductivity cell C2, and a fail-safe arrangement to prevent electrical heater failure on water flow stoppage. It is preferred that the metals used in the apparatus of the invention be made of material, such as stainless steel, resistant to erosion and corrosion of flowing water at high temperatures. Such erosion and corrosion will contaminate the water being tested.

If desired, the flow cell $C_1$ and its associated recorder 19 may be eliminated in which case the tube 16 from the resin bed 12 will be connected directly to the flowmeter F. The hydrogen exchange resin should preferably contain a coloring dye which changes color as the resin becomes exhausted. Observation of the degree of color change in the resin bed as observed through the transparent lucite column 13 indicates when the resin should be replaced.

The apparatus of the invention was constructed, installed and tested successfully at the Crawford Station of Commonwealth Edison, Chicago. Since the conductivity results were obtained at constant temperature and free of $CO_2$ and amine interferences, precise measurement of anion contamination was observed. The present invention provides continuous measurements and should enable the recording of low levels of inorganic anions, for example 5-10 ug/l $Cl^-$ and/or $SO_4^=$ (micrograms per liter of chlorides and/or sulfate) and lower in relatively low pressure make-up and condensate having a temperature below atmospheric boiling temperature. In this apparatus which was constructed and tested, the overall height of the reboiler 20 to the vent 24 was about 30". Level 23 was about 16" from the bottom. The outer diameter was about 1½". The reboiler chamber was made of stainless steel and is preferably sheathed in ½" insulation to retain heat in the reboiler. The resin bed 12 was a column about 10" high and 2" in diameter.

What is claimed is:

1. The method of continuously detecting low levels of chloride, sulfate, phosphate, nitrate and other inorganic ions of the order of 5 ug/l and less in relatively low pressure condensate having a temperature of approximately 40° C. or lower, which comprises passing a sample of said condensate at a substantially constant pressure of approximately 100 lbs. psi or less but above atmospheric pressure with a flow rate of approximately 175 ml/min through a bed of hydrogen exchange resin, electrically heating the effluent from said resin bed to raise its temperature to the atmosphere boiling temperature, automatically regulating said heating to maintain the temperature of said heated effluent constant at said atmospheric boiling temperature, driving off carbon dioxide and other gases from the heated effluent, and continuously measuring and recording the conductivity of the heated effluent.

2. The method of claim 1 which includes stopping said electrical heating on failure of condensate flow.

3. The method of claim 2, including the step of regulating the heating of the effluent from the resin as a function of the temperature of the condensate supplied to said resin.

4. Apparatus for determining the purity of relatively low pressure condensate having a temperature of the order of 40° C. or lower, comprising a hydrogen resin bed, an inlet supplying a sample of low pressure condensate to said bed, means between said bed and inlet for maintaining the pressure of said condensate substantially constant, an electric reboiler and means for maintaining a liquid level therein, means defining a fluid communication path between the output of said resin bed and the interior of said reboiler for passing the effluent from said resin bed to said reboiler, an electrical heating element for heating the resin effluent in said reboiler to atmospheric boiling temperature, a vent in said reboiler for discharging carbon dioxide and other gases released from the boiling effluent in said reboiler, means defining a fail-safe device responsive to a drop in the liquid effluent level in said reboiler, a heat control device for regulating the amount of voltage or current flowing into said electrical heating element, said heat control device being coupled between said fail-safe device and said heating element for cutting off the current in said heating element upon an appreciable drop in the effluent supplied to said reboiler, and a flow type conductivity cell in fluid communication with the effluent in said reboiler for continuously measuring the degree of contamination in said condensate.

5. Apparatus according to claim 4, including means coupled to said heat control device for regulating the amount of electric energy supplied to said heating element to assure a constant atmospheric boiling temperature of the water in said reboiler.

6. Apparatus according to claim 5, including means in the output flow path from said conductivity cell for assuring a constant water level in said electric reboiler.

7. Apparatus according to claims 4 or 5, wherein said means for maintaining the pressure of said condensate substantially constant includes a flow regulating valve.

8. Apparatus according to claim 4, wherein said resin bed is approximately 10" high and 2" in diameter, said reboiler is approximately 30" high overall, and said electrical heating element is U-shaped.

9. An electric reboiler analyzer of test water having a relatively low pressure and a temperature of approximately 40° C. or less, comprising a reboiler, an electric heating element in said reboiler, a hydrogen exchange resin bed, an inlet conduit supplying said test water to said bed, a tube supplying the effluent from said bed to said reboiler, a heat control device coupled to said heating element for regulating the amount of current supplied to said heating element to assure that the water in said reboiler is heated to a constant atmospheric boiling temperature, means in fluid coupling relation to said reboiler for maintaining the water in said reboiler at a constant level, means coupled to said heat control device and responsive to a drop in said constant level for shutting off the electric current supplied to said electric heating element, a conduit in fluid communication with the interior of said reboiler for dissipating steam and air bubbles generated by the heated water in said reboiler, and means also in fluid communication with said reboiler for continuously measuring the conductivity of the heated water in said reboiler.

10. An electric reboiler according to claim 9, including means associated with said inlet conduit for regulating the flow of test water to said hydrogen exchange bed, a temperature sensor coupled to said inlet conduit for sensing the temperature of said test water, and a connection from said sensor to said heat control device.

11. An analyzer according to claim 9, including means for subtracting the conductivity of pure water from the conductivity measurement of the heated water to thereby indicate the chloride and sulfate content of the heated water.

12. Electrically heated detecting and measuring apparatus for determining the purity of relatively low pressure condensate having a temperature of the order of 40° C. or lower, comprising a hydrogen exchange resin bed, an inlet conduit for supplying a sample of said condensate to said bed, means between said bed and inlet for maintaining the pressure of said condensate sample substantially constant, a water reboiler with liquid level control means, conduit means between the output of said resin bed and the interior of said reboiler for passing the effluent from said resin bed to said reboiler, an electrical heating element in said reboiler for heating the resin effluent to atmospheric boiling temperature, a vent in said reboiler which is open to the atmosphere for discharging carbon dioxide and other gases released from the boiling water in said reboiler, means defining a fail-safe device responsive to a drop in the effluent level in said reboiler, a heat control device coupled between said fail-safe device and said heating element for removing the current from said heating element upon an appreciable drop in the effluent supplied to said reboiler, a flow-type conductivity cell in fluid communication with the effluent in said reboiler, and recording means coupled to said cell for automatically subtracting the conductivity of pure water from the conductivity measurement of said cell to thereby indicate the chloride and sulfate content of the effluent flowing through said cell.

13. Electrically heated portable measuring apparatus for determining the purity of relatively low pressure condensate having a temperature of the order of 40° C. and lower, comprising a bed of hydrogen exchange resin, an inlet for supplying said condensate to said bed, means including a pressure regulator and a valve in series therewith between said inlet and said bed for maintaining the pressure of the condensate substantially constant, an electric reboiler having a container made of a material which is resistant to erosion and corrosion, a tubular fluid communication path between the output of said resin bed and the interior of said container for passing the effluent from said resin bed to said reboiler, an electric heating element within said container of said electric reboiler for heating the resin effluent in said reboiler to atmospheric boiling temperature, means defining a fail-safe device responsive to a drop in the effluent level in said reboiler coupled to said electric heating element, and means coupled to the output of said container through which liquid from said reboiler flows for measuring the degree of contamination in said condensate.

14. Apparatus according to claim 13, wherein said reboiler is arranged in a vertical position and the container of said reboiler is sheathed in insulation, one end of said vent being open to the atmosphere.

15. Portable apparatus as defined in claim 13, including flow-type conductivity cell in said tubular fluid communication path which extends between the output of said resin bed and the interior of said reboiler, and a recorder coupled to said last cell.

16. Electrically heated relatively light weight, compact, portable measuring apparatus for determining the purity of relatively low pressure condensate having a temperature of the order of 40° C. or lower, comprising a hydrogen resin bed containing a coloring die located within a transparent container, an inlet for supplying said condensate to said bed, means between said bed and said inlet for maintaining the pressure of the condensate substantially constant, an electric reboiler with liquid level control means, said reboiler having a container made of a material which is resistant to erosion and corrosion, a tubular fluid communication path between the output of said resin bed and the interior of said reboiler for passing the effluent from said resin bed to said reboiler, an electrical heating element within the container of said electric reboiler for heating the resin effluent in said reboiler to atmospheric boiling temperature, a vent in said reboiler for discharging carbon dioxide and other gases released from the boiling effluent in said reboiler, means defining a fail-safe device responsive to a drop in the effluent level in said reboiler, a heat control device coupled between said fail-safe device and heating element for cutting off the current in said heating element upon an appreciable drop in the effluent supplied to the reboiler, a temperature sensing device coupled between said inlet and said heat control device for continuously controlling or regulating the voltage or current in said heating element to assure the proper heat for constant atmospheric boiling temperature of the effluent in said reboiler, and a flow-type conductivity cell fluid-coupled to the interior of said reboiler through which the effluent from said reboiler flows for continuously measuring the degree of contamination of said condensate.

17. Apparatus according to claim 16 including manually adjustable means in series with said cell for providing a constant level of heated effluent in said reboiler.

18. Apparatus according to claim 16 including a tube coupled at one end to the fluid coupling path of said cell and open at its other end to the atmosphere for providing an outlet to the atmosphere for flash steam and air bubbles.

* * * * *